United States Patent [19]

Ogura et al.

[11] Patent Number: 5,512,644
[45] Date of Patent: Apr. 30, 1996

[54] AMPHOLYTIC POLYMER CAPABLE OF ABSORBING AQUEOUS ELECTROLYTE SOLUTION

[75] Inventors: Kuniyoshi Ogura, Okayama; Kouji Sasaki, Suita, both of Japan

[73] Assignee: Toyo Boseki Kabushiki Kaisha, Osaka, Japan

[21] Appl. No.: 302,428

[22] Filed: Sep. 8, 1994

[30] Foreign Application Priority Data

Sep. 8, 1993 [JP] Japan .................. 5-223532
Mar. 8, 1994 [JP] Japan .................. 6-037115
Jul. 12, 1994 [JP] Japan .................. 6-160245

[51] Int. Cl.$^6$ .............. C08F 226/06; C08F 228/02; C08F 20/58
[52] U.S. Cl. .............. 526/258; 526/263; 526/265; 526/288; 526/303.1; 526/304; 526/311; 526/312
[58] Field of Search .............. 526/258, 263, 526/265, 288, 303.1, 310, 312, 304, 311

[56] References Cited

U.S. PATENT DOCUMENTS

| | | | |
|---|---|---|---|
| 2,846,417 | 8/1958 | Shacklett | 526/270 |
| 3,493,547 | 2/1970 | Szita et al. | 526/288 |
| 4,215,028 | 7/1980 | Mizuguchi et al. | 526/258 |
| 5,130,391 | 7/1992 | Ahmed et al. | 526/288 |
| 5,225,506 | 7/1993 | Ahmed et al. | 526/258 |
| 5,243,008 | 9/1993 | Ahmed et al. | 527/309 |
| 5,256,751 | 10/1993 | Vanderlaan | 526/304 |
| 5,270,382 | 12/1993 | Ahmed et al. | 526/258 |

OTHER PUBLICATIONS

"Polyampholytes", Encyclopedia of Polymer Science and Engineering, 2nd Ed., vol. 11, pp. 516–519 Mark et al. eds. Wiley, New York 1988.

Itoh et al., *Solution and membrane properties of zwitterionic polymers*, Makromol. Chem. 187, 1986, pp. 1691–1697.

Salamone et al., *Preparation of inner salt polymers from vinylimidazolium sulphobetaines*, Polymer, 1977, vol. 18, pp. 1058–1063.

Salamone et al., *Aqueous solution properties of a poly(vinyl imidazolium sulphobetaine)*, Polymer, 1978, vol. 19, pp. 1157–1163.

Soto et al., *Poly(sulphopropylbetaines):2. Dilute solution properties*, Polymer, 1984, vol. 25, pp. 254–262.

Liaw et al., *Aqueous Solution Properties of Poly[3–Dimethyl (Methacryloyloxyethyl) Ammonium Propane Sulfonate]*, Journal of Applied Polymer Science, 1987., vol. 34, pp. 999–1011.

Kathmann et al., *Water–Soluble Polymers. 60. Synthesis and Solution Behavior of Terpolymers of . . .*, Macromolecules, 1994, vol. 27, pp. 3156–3161.

*Primary Examiner*—Tae Yoon
*Attorney, Agent, or Firm*—Foley & Lardner

[57] ABSTRACT

There is disclosed an ampholytic polymer capable of absorbing aqueous electrolyte solutions, which is obtainable by polymerization of a monomer mixture including (A) at least 10 mol % of an ampholytic vinyl monomer, with the proviso that when the monomer (A) has no self-crosslinkability, the amount of monomer (A) is in the range of 10 to 99.995 mol %. The monomer mixture may further include (B) 90 mol % or less of a non-ampholytic vinyl monomer and (C) 1 mol % or less of a crosslinkable monomer, with the proviso that the total amount of monomers (A), (B) and (C) is 100 mol % and when the monomer (A) has no self-crosslinkability, the amount of monomer (C) is in the range of 0.005 to 1 mol %.

6 Claims, No Drawings

AMPHOLYTIC POLYMER CAPABLE OF ABSORBING AQUEOUS ELECTROLYTE SOLUTION

FIELD OF THE INVENTION

The present invention relates to an ampholytic crosslinked polymer having ampholytic side-chain groups, which exhibits high absorption capacity for various aqueous electrolyte solutions. The ampholytic polymer of the present invention is particularly useful for many applications requiring the absorption of aqueous electrolyte solutions.

BACKGROUND OF THE INVENTION

Water-absorptive resins which can absorb several hundred times their own weight of water can find wide applications such as absorbents used in paper diapers or sanitary products; water-retaining materials, soil-conditioners and water-stop materials for agricultural or horticultural use. As the water-absorptive resin, for example, there have been known starch-acrylonitrile graft copolymer hydrolysate; starch-acrylic acid graft copolymers; carboxycellulose crosslinked polymers; vinyl acetate-methyl acrylate copolymer hydrolyzate; and polyacrylic acid salt crosslinked polymers.

These water-absorptive resins have quite excellent absorption capacity for pure water and deionized water: however, they have a disadvantage that the absorption capacity is decreased for aqueous electrolyte solutions such as see water, brine, blood, sweat and urine. In particular, the absorption capacity is remarkably decreased for aqueous electrolyte solutions of high concentration, such as see water, or aqueous solutions of polyvalent metal salts, which causes some limitation of applications.

To increase the absorption capacity for aqueous electrolyte solutions, there have been proposed various salt-resistant absorbents, for example, crosslinked polymers containing sulfoalkyl(meth)acrylate (see JP-A 61-36309/1986) and crosslinked copolymers of a (meth)acrylate derivative having polyether side chains and a monomer having a sulfonic group (JP-A 62-266140/1987). However, these water-absorptive resins still have decreased absorption capacity for aqueous electrolyte solutions of high concentration, such as see water, or aqueous solutions of polyvalent metal salts.

SUMMARY OF THE INVENTION

Under these circumstances, the present inventors have intensively studied a polymer having high absorption capacity for aqueous electrolyte solutions. As the result, they found that such a polymer can be obtained by polymerization of a particular monomer mixture, thereby completing the present invention.

Thus, the present invention provides an ampholytic polymer capable of absorbing aqueous electrolyte solutions, which is obtainable by polymerization of a monomer mixture comprising (A) at least 10 mol % of an ampholytic vinyl monomer, with the proviso that when the monomer (A) has no self-crosslinkability, the amount of monomer (A) is in the range of 10 to 99.995 mol %. The monomer mixture may further comprise (B) 90 mol % or less of a non-ampholytic vinyl monomer and (C) 1 mol % or less of a crosslinkable monomer, with the proviso that the total amount of monomers (A), (B) and (C) is 100 mol % and when the monomer (A) has no self-crosslinkability, the amount of monomer (C) is in the range of 0.005 to 1 mol %.

The development of a water-absorptive resin having excellent absorption capacity for aqueous electrolyte solutions, particularly aqueous electrolyte solutions of high concentration and aqueous solutions of polyvalent metal salts, makes it possible to expand the range of its application into various fields to which conventional water-absorptive resins cannot be applied. With an increase in the absorption capacity, the amount of resin to be required for absorbing aqueous electrolyte solutions is drastically decreased, which saves material resources and cuts down the expenses for users.

DETAILED DESCRIPTION OF THE INVENTION

The ampholytic polymer of the present invention has excellent absorption capacity for various aqueous electrolyte solutions. As used herein, the term "electrolyte" refers to a substance which can be dissolved in water or other solvents to form a solution capable of effecting ionic conduction. As used herein, the term "aqueous electrolyte solution" refers to an aqueous solution in which at least one kind of such a substance is dissolved.

The ampholytic polymer capable of absorbing aqueous electrolyte solutions according to the present invention can be obtained by polymerization of a monomer mixture comprising (A) at least 10 mol % of ampholytic vinyl monomer, with the proviso that when the monomer (A) has no self-crosslinkability, the amount of monomer (A) is in the range of 10 to 99.995 mol%. The monomer mixture may further comprises (B) 90 mol % or less of a non-ampholytic vinyl monomer and (C) 1 mol % or less of a crosslinkable monomer with the proviso that the total amount of monomers (A), (B) and (C) is 100 mol % and when the monomer (A) has no self-crosslinkability, the amount of monomer (C) is in the range of 0.005 to 1 mol %.

The ampholytic vinyl monomer (A) has both an anionic group and a cationic group in the same monomer unit. The monomer (A) can be used alone or in combination.

The term "anionic group" as used herein refers to a group having the property of causing ionization in an aqueous medium to become an anion, such as a carboxyl group, a sulfonic group, a sulfuric ester group and a phosphoric group. The term "cationic group" as used herein refers to a group having the property of causing ionization in an aqueous medium to become a cation such as an amino group, a secondary amino group, a tertiary amino group and a quaternary ammonium group.

The ampholytic vinyl monomer (A) is preferably selected from the group consisting of:

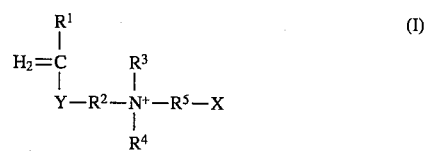

wherein $R^1$ is hydrogen or methyl; $R^2$ is a direct bond, or straight-chain or branched $C_1$–$C_6$ alkylene or hydroxyalkylene; $R^3$ and $R^4$ are independently methyl or ethyl; $R^5$ is straight-chain or branched $C_1$–$C_{10}$ alkylene or hydroxyalkylene; X is —COO⁻ or —SO₃⁻; and Y is an ester or amide linkage,

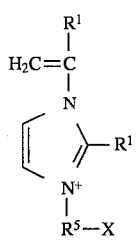

wherein $R^1$, $R^5$ and X are each as defined above;

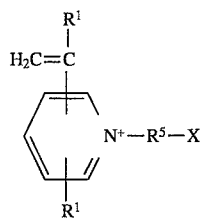

wherein $R^1$, $R^5$ and X are each as defined above; and

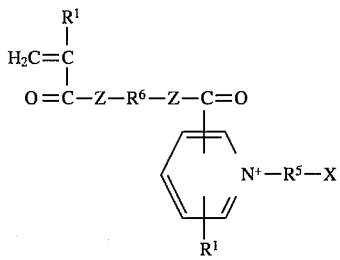

wherein $R^1$, $R^5$ and X are each as defined above; $R^6$ is straight-chain or branched $C_1$-$C_6$ alkylene or hydroxyalkylene; and Z is —O— or —NH—.

In the formulae (III) and (IV), the substituents (i.e., $R^1$ and polymerizable substituent) on the pyridine ring may take any possible position.

When a (meth)acrylamide monomer of the formula (I) wherein Y is amido; $R^3$ and $R^4$ are both methyl; and $R^5$ is $C_1$-$C_3$ alkylene is used as the ampholytic vinyl monomer (A), it is possible to obtain an ampholytic polymer having higher absorption capacity for aqueous electrolyte solutions. In other words, the absorption capacity is improved because the hydrophilicity of the polymer is increased by the presence of a strongly hydrophilic amide linkage introduced into the side-chain group of the monomer.

The ampholytic vinyl monomer (A) of the present invention is commonly known as a sulfobetaine or carboxybetaine monomer. The monomer of the formula (I), (II), (III) or (IV) is called either a sulfobetaine monomer when X is —$SO_3^-$ or a carboxy-betaine monomer when X is —$COO^-$. In many cases, the sulfobetaine monomer is obtained by reaction of the corresponding tertiary amine monomer with a sulfone. For example, dimethyl-(2-methacryloyloxyethyl)-1-(3-sulfopropyl)ammonium internal salt can be obtained by reaction of N,N-dimethylaminoethylmethacrylate with 1,3-propanesultone in dimethylformamide at 30° C. for 7 days. The sulfobetaine monomer can also be obtained by reaction of the corresponding tertiary amine monomer with a condensate of an aldehyde or ketone and acidic sodium sulfite; by reaction of the corresponding tertiary amine monomer with a haloalkanesulfonic acid; or by conversion of a hydroxyl-containing quaternary ammonium monomer into a sulfuric ester. In addition, sulfobetaine monomers such as 1-vinyl-3-(3-sulfopropyl)imidazolium internal salt, 1-vinyl-2-methyl-3-(3-sulfopropyl)imidazolium internal salt, 1-vinyl-2-methyl-3-(4-sulfobutyl)imidazolium internal salt, 1-vinyl-3-(2-sulfobenzyl)imidazolium internal salt, 2-vinyl-1-(3-sulfopropyl)pyridinium internal salt, 2-methyl-5-vinyl-1-(3-sulfopropyl)pyridinium internal salt, 4-vinyl-1-(3-sulfopropyl)pyridinium internal salt, diethyl-(2-methacryloyloxyethyl)-1-(3 -sulfopropyl)ammonium internal salt, 3-{3-[2-(methacryloyloxy)ethoxycarbonyl]pyridinio} propanesulfonate internal salt and dimethyl-(2-acryloyloxyethyl)-1-(3-sulfopropyl)ammonium internal salt can preferably be used as the ampholytic vinyl monomer (A) of the present invention.

The carboxybetaine monomer can be obtained by reaction of the corresponding tertiary amine monomer with a monohaloalkylcarboxylic acid. For example, N,N-dimethyl-N-(2-methacryloyloxyethyl)-N-(carboxymethyl)ammonium internal salt can be obtained by reaction of dimethylaminoethylmethacrylate with sodium monochloroacetate in methanol. The carboxybetaine monomer of the present invention can also be obtained by reaction of the corresponding tertiary amine monomer with a cyclic ester such as propiolactone. In addition, carboxybetaine monomers such as N,N-dimethyl-N-(2-methacryloyloxyethyl)-N-(carboxyethyl)ammonium internal salt, N,N-dimethyl-N-(2-acryloyloxyethyl)-N-(carboxymethyl)ammonium internal salt and N,N-dimethyl-N-(2-acryloyloxyethyl)-N-(carboxyethyl)ammonium internal salt can preferably be used as the ampholytic vinyl monomer (A) of the present invention.

Further, as the ampholytic vinyl monomer (A) of the (meth)acrylamide type having an amide linkage, sulfobetaine monomers such as N,N-dimethyl-N-(3-acrylamidopropyl)-N-( 3-sulfopropyl)ammonium internal salt and N,N-dimethyl-N-(3-methacrylamidopropyl)-N-( 3-sulfopropyl)ammonium internal salt; and carboxybetaine monomers such as N,N-dimethyl-N-(3-acrylamidopropyl)-N-(carboxymethyl)ammonium internal salt, N,N-dimethyl-N-(3-methacrylamidopropyl)-N-(carboxymethyl)ammonium internal salt, N,N-dimethyl-N-(3-acrylamidopropyl)-N-(2-carboxyethyl)ammonium internal salt and N,N-dimethyl-N-(3-methacrylamidopropyl)-N-(2-carboxyethyl)ammonium internal salt can more preferably be used in the present invention.

Various polymers having ampholytic functional groups which have been incorporated by polymer reaction to these polymers are also included in the present invention. More particularly, ampholytic polymers having high absorption capacity for aqueous electrolyte solutions can also be obtained by incorporation of ampholytic functional groups through the polymer reaction of a tertiary amino-containing polymer with a sulfone, monohaloalkylcarboxylic acid or cyclic ester; thorough the reaction of a polymer with a compound having an ampholytic functional group; or through the graft polymerization of a polymer with the ampholytic vinyl monomer (A).

The amount of ampholytic vinyl monomer (A) contained in the monomer mixture at the time of polymerization is in the range of from 10 mol % to 100 mol %, preferably from 30 mol % to 100 mol %, in which case ampholytic polymers having high absorption capacity for aqueous electrolyte solutions can be obtained. Amounts less than 10 mol % are not preferred because the resultant ampholytic polymer has insufficient absorption capacity for aqueous electrolyte solution. When the ampholytic vinyl monomer (A) has self-crosslinkability, it is not necessary to use the crosslinkable monomer (C), in which case the ampholytic vinyl monomer (A) may be used in the amount of 100 mol %. To the contrary, when the ampholytic vinyl monomer (A) has no self-crosslinkability, it is desirable to use the crosslinkable monomer (C), in which case the ampholytic vinyl monomer (A) may be used in an amount of 10 to 99.995 mol % and the crosslinkable monomer (C) may be used in an amount of at least 0.005 mol %.

In the present invention, any kind of the non-ampholytic vinyl monomer (B) may be used, so long as the absorption capacity of the resultant ampholytic polymer is not deteriorated. If there is no need to use it, it may be eliminated from the monomer mixture. In other words, the non-ampholytic vinyl monomer (B) can conveniently be selected from radical-polymerizable vinyl monomers and used for the purpose of improving the physical properties, such as strength, of the resultant ampholytic polymer depending on its application.

The non-ampholytic vinyl monomer (B) is preferably selected from water-soluble monomers having a hydrophilic functional group for the purpose of increasing the absorption capacity of the resultant ampholytic polymer. Examples of the hydrophilic functional group are a carboxyl group, an amido group, a hydroxyl group, a sulfonic group, a phosphoric group, an amino group, a quaternary ammonium group and a polyethylene glycol group. In addition, it is also possible to use various monomers into which a hydrophilic functional group can readily be introduced by hydrolysis or the like. Examples of the monomer which has a hydrophilic functional group or which can readily be given a hydrophilic functional group are acrylic acid and its alkali salts, methacrylic acid and its alkali salts, itaconic acid, acrylonitrile, alkyl acrylates, alkyl methacrylates, acrylamide, methacrylamide, N-substituted alkylacrylamides, hydroxyethyl acrylate, hydroxyethyl methacrylate, hydroxypropyl acrylate, hydroxypropyl methacrylate, hydroxyethyl acrylamide, vinyl acetate, vinylsulfonic acid and its alkali salts, methallylsulfonic acid and its alkali salts, styrenesulfonic acid and its salts, 2-acrylamido-2-methylpropanesulfonic acid and its alkali salts, 2-methacryloyloxyethanesulfonic acid its alkali salts, mono(2-acryloyloxyethyl) acid phosphate, mono(2-methacryloyloxyethyl) acid phosphate, 3-methacrylamidopropyldimethylamine and its salts, 2-methacryloyloxyethyldimethylamine and its salts, 2-methacryloyloxyethyldiethylamine and its salts, 3-methacrylamidopropyltnmethylammonium chloride, N-vinyl-2-pyrrolidone, polyethylene glycol methacrylate and polyethylene glycol acrylate. These monomers can be used alone or in combination.

The amount of non-ampholytic vinyl monomer (B) contained in the monomer mixture at the time of polymerization is preferably in the range of from 0 to 90 mol %, more preferably from 0 to 70 mol %, for the purpose of giving the absorption capacity for electrolyte solutions.

To provide a water-absorptive resin which can absorb an aqueous medium and then remain swollen without being dissolved in the medium, it is necessary to introduce crosslinked structure into the ampholytic polymer by covalent, or hydrogen bonds. In the present invention multi functional radical-polymerizable monomers such as divinyl compounds can be used as the crosslinkable monomer (C) to introduce crosslinked structure into the ampholytic polymer. As the multifunctional radical-polymerizable monomer, bisacrylamides, di(meth)acrylic esters and dially compounds can preferably be used in the present invention.

Examples of the multifunctional radical-polymerizable monomer are N,N-diallylmethacrylamide, diallylamine, N,N-bisacrylamidoacetic acid, methyl N,N'-bisacrylamidoacetate, N,N'-methylenebisacrylamide, N,N-benzylidenebisacrylamide, diallyl succinate, ethylene glycol diacrylate, diethylene glycol diacrylate, triethylene glycol diacrylate, tetraethylene glycol diacrylate, polyethylene glycol diacrylate, neopentyl glycol diacrylate, 1,6-hexanediol diacrylate, ethylene glycol dimethacrylate, diethylene glycol dimethacrylate, triethylene glycol dimethacrylate, tetraethylene glycol dimethacrylate, polyethylene glycol dimethacrylate, 1,4-butanediol dimethacrylate, 1,3-butanediol dimethacrylate. 1,6-hexanediol dimethacrylate, 2-hydroxy-3-acryloyloxypropylmethacrylate, glycerol dimethacrylate, neopentyl glycol dimethacrylate and diallylacrylamide. These monomers can preferably be used in the present invention.

As another method for introduction of crosslinked structure into the ampholytic polymer, there can be mentioned crosslinking treatment with a monomer having a post-crosslinkable functional group after the polymerization. If such a monomer which can be used for the crosslinking treatment is employed as the crosslinkable monomer (C) in the present invention. A compound is sometimes used which can be chemically bonded with the monomer (C) to form crosslinked structure, and such a compound is referred to as a crosslinking aid. If a monomer which can be self-crosslinked by heating or the like is used, it is not necessary to use a crosslinking aid. Further, the crosslinkable monomer (C) may be the same monomer as the non-ampholytic vinyl monomer (B), in which case the crosslinkable monomer (C) is considered as a monomer component among the non-ampholytic monomers (B), which has made a contribution to the crosslinked structure alter the crosslinking treatment. As the monomer which can be used for the crosslinking treatment. Monomers having a carboxyl, amido, nitrile, methylol, glycidyl, hydroxyl or imino group; and acid anhydride monomers can preferably be used in the present invention. Examples of the monomer are acrylic acid, methacrylic acid, itaconic acid, acrylamide, methacrylamide, acrylonitrile, N-methylolacrylamide, glycidyl acrylate, glycidyl methacrylate. Hydroxyethyl acrylate, hydroxyethyl methacrylate, hydroxyethyl acrylamide, hydroxypropyl acrylate, hydroxypropyl methacrylate and aziridinyl methacrylate.

As the crosslinking aid, for example, if the crosslinkable monomer (C) has a carboxyl group, multifunctional compounds having two or more functional groups, such as hydroxyl, epoxy, amino and methylol groups, which can react with the carboxyl group to form a chemical bond, can be used. Example of such a multifunctional compound are ethylene glycol, propylene glycol, glycerol, glycidyl alcohol, diglycidyl ether, glycerol triglycidyl ether, ethylene glycol diglycidyl ether, ethanolamine, ethylenediamine, propylenediamine, polyethylene glycol, polyvinyl alcohol, trimethylolmelamine, pentaerythritol, trimethylolpropane, polyethyleneimine and urea. Further, crosslinking reaction with formaldehyde or multivalent metal ions can also be employed.

If the crosslinkable monomer (C) has a hydroxyl group, multifunctional compounds having two or more functional groups, such as carboxyl, acid anhydride, aldehyde and isocyanate groups, which can react with the hydroxyl group to form a chemical bond, can be used as the crosslinking aid. Examples of such a multifunctional compound are malonic acid, succinic acid, glutaric acid, malic acid, propane-1,2, 3-tricarboxylic acid and anhydrides or these acids, glyoxal, glutaraldehyde, hexamethylenediisocyanate and cyclohexanediisocyanate.

If the hydroxyl groups can form crosslinked structure by hydrogen bonds with other hydroxyl groups or carboxyl groups, there is no need to use a crosslinking aid. For example, vinyl acetate, a (meth)acrylic ester or the like is used as the non-ampholytic vinyl monomer (B) to form a hydroxyl or carboxyl group by hydrolysis, in which case microcrystalline structure through the hydrogen bond serves as a crosslinking point to provide an ampholytic polymer capable or absorbing water and then remaining swollen without particularly introducing any crosslinked structure through the covalent bond. Such a method for introduction of crosslinked structure can also be used in the present invention.

The introduction of crosslinked structure can also be achieved by crosslinking through the formation of an acid anhydride from carboxyl groups or from a carboxyl group and a hydroxyl group or from hydroxyl groups using a dehydration catalyst or by heating; or by crosslinking through ester or ether linkages.

If the crosslinkable monomer (C) has a nitrile group, multifunctional compounds having two or more functional groups, such as an amino group, which can react with the nitrile group to form a chemical bond, can be used as the crosslinking aid. Examples of such a multifunctional compound are hydrazine, ethylenediamine, propylenediamine, butylenediamine, pentamethylenediamine, hexamethylenediamine and amino-terminated polyethylene glycol.

The amount of crosslinkable monomer (C) contained in the monomer mixture at the time of polymerization is preferably at least 0.005 mol %, more preferably at least 0.01 mol % because the polymer having absorbed an aqueous medium is not dissolved in the medium and has no flowability. When the ampholytic vinyl monomer (A) has self-crosslinkability, it is not necessary to use the crosslinkable monomer (C). The amount of crosslinkable monomer (C) is preferably 1 mol % or less, more preferably 0.1 mol % or less, because the absorption capacity is decreased with an increase in the amount of crosslinkable monomer (C) contained in the polymer. If the non-ampholytic vinyl monomer (B) is the same monomer as the crosslinkable monomer (C), the amount of crosslinkable monomer (C) contained in the monomer mixture is adjusted in accordance with the amount of non-ampholytic vinyl monomer (B).

The ampholytic polymer of the present invention may be prepared by any of radical polymerization techniques which have been widely used. That is, any technique or bulk polymerization, precipitation polymerization in an aqueous medium, suspension polymerization, reverse-phase suspension polymerization, emulsion polymerization or solution polymerization may be used, and it can conveniently be selected in view of the form of a polymer to be obtained, depending on its application. In general, polymerization systems using water as a medium are desirable from an economical and environmental points of view. The radical formation can be achieved by the use of a radical polymerization catalyst or by irradiation or exposure to electron or ultraviolet rays. Examples of the radical polymerization catalyst are free-radical initiators such as peroxides (e.g., hydrogen peroxide, benzoyl peroxide and cymene hydroperoxide); azo compounds (e.g., azobisisobutyronitrile and azobiscyanovaleric acid; and persulfates (e.g., ammonium persulfate and potassium persulfate); as well as redox initiators consisting of a combination of the above free-radical initiator and a reducing agent such as sodium hydrogensulfite or L-ascorbic acid. Examples of the polymerization medium are water, aqueous electrolyte solutions, methanol, acetone and dimethylformamide, although it may conveniently be selected depending on the polymerization technique employed. With respect to the conditions for polymerization, they are not particularly limited and may conveniently be selected depending on the polymerization technique employed, so long as the polymerization can provide an ampholytic polymer capable of absorbing aqueous electrolytic solutions.

The reason why the ampholytic polymer of the present invention has high absorption capacity for aqueous electrolyte solutions has not sufficiently been made clear but it is probably as follows. From the fact that homopolymers of a non-crosslinked linear sulfobetaine monomer cannot be dissolved in pure water but can be dissolved in aqueous electrolyte solutions of a certain fixed or higher concentration, the ionic bond between the sulfonic group and the quaternary ammonium group, both of which form a salt in the ampholytic side-chain group, is broken by the presence of low-molecular ions, so that the polymer chain is stretched to cause the polymer dissolution. For this reason, even in the case of a polymer having crosslinked structure, it seems to be swollen with aqueous electrolyte solutions to exhibit high absorption capacity. In contrast, homopolymers of a carboxybetaine monomer exhibit good solubility both in pure water and in aqueous electrolyte solutions. For this reason, even in the case of a polymer having crosslinked structure, it seems to absorb aqueous electrolyte solutions with high efficiency.

EXAMPLES

The present invention will be further illustrated by the following examples, which are not to be construed to limit the scope thereof.

As the ampholytic vinyl monomer (A), sulfobetaine monomers such as N,N-dimethyl-(2-methacryloyloxyethyl)-1-(3-sulfopropyl)ammonium internal salt (DMEPS), N,N-dimethyl-(2-acryloyloxyethyl)-1-(3-sulfopropyl)ammonium internal salt (DAEPS), N,N-dimethyl-N-(3-methacrylamidopropyl)-N-(sulfopropyl)ammonium internal salt (DMPPS) or N,N-dimethyl-N-(3-acrylamidopropyl)-N-(3-sulfopropyl)-ammonium internal salt (DAPPS); and carboxybetaine monomers such as N,N-dimethyl-N-(3-acrylamidopropyl)-N-(carboxymethyl)ammonium internal salt (DAPMB), N,N-dimethyl-(3-methacrylamidopropyl)-N-(carboxymethyl)ammonium internal salt (DMPMB) or N,N-dimethyl-N-(2-methacryloyloxyethyl)-N-(carboxymethyl)ammonium internal salt (DMEMB) were used.

All the sulfobetaine monomers, DMEPS, DAEPS, DMPPS and DAPPS, were prepared as follows. A mixture of 1 mol of a tertiary amine monomer corresponding to each of these monomers and 1.2 mol of 1,3-propanesultone was stirred in dimethylformamide at 30° C. for 7 days. The precipitated products were collected by filtration and then dissolved in methanol. followed by reprecipitation with ethyl acetate purification.

DAPMB was purchased from Kojin Co., Ltd. DMPMB and DMEMB were prepared by reacting a tertiary amine monomer corresponding to each of these monomers and sodium monochloroacetate in methanol at 60° C.

As the non-ampholytic vinyl monomer (B), acrylic acid (AA), acrylamide (AAm) and 2-acrylamido-2-methylpropanesulfonic acid (AMPS) were used. As the crosslinkable monomer (C), N,N'-methylenebisacrylamide (MBAAm) was used.

A monomer mixture containing given amounts of monomers was dissolved, together with ammonium persulfate (APS) as an initiator in an amount of 0.3 mol %, based on the total amount of monomers in deionized water (total monomer concentration was 30% by weight), and polymerization was effected at 90° C. for 2 hours, followed by drying and grinding, resulting in a powdered polymer. Various polymers containing or not containing the ampholytic vinyl monomer (A), which are not included within the scope of the present invention, were also prepared in the same manner as described above. The amounts of monomers contained in the monomer mixture, i.e., the monomer composition is shown in Table 1.

TABLE 1

| | | Monomer composition (mol %) | | | | | | | | | | |
|---|---|---|---|---|---|---|---|---|---|---|---|---|
| | | Monomer (A) | | | | | | | Monomer (B) | | | Monomer (C) |
| X | Polymer | DMEPS | DAEPS | DAPPS | DMPPS | DAPMB | DMPMB | DMEMB | AA | AAm | AMPS | MBAAm |
| X | 1 | 99.998 | — | — | — | — | — | — | — | — | — | 0.002 |
| O | 2 | 99.995 | — | — | — | — | — | — | — | — | — | 0.005 |
| O | 3 | 99.99 | — | — | — | — | — | — | — | — | — | 0.01 |
| O | 4 | 99.9 | — | — | — | — | — | — | — | — | — | 0.1 |
| O | 5 | — | 99 | — | — | — | — | — | — | — | — | 1 |
| X | 6 | — | 98 | — | — | — | — | — | — | — | — | 2 |
| O | 7 | — | 50 | — | — | — | — | — | 49.98 | — | — | 0.02 |
| O | 8 | — | 30 | — | — | — | — | — | 69.98 | — | — | 0.02 |
| O | 9 | — | 10 | — | — | — | — | — | 89.98 | — | — | 0.02 |
| X | 10 | — | 5 | — | — | — | — | — | 94.98 | — | — | 0.02 |
| O | 11 | — | 50 | — | — | — | — | — | — | 49.98 | — | 0.02 |
| O | 12 | — | — | 99.95 | — | — | — | — | — | — | — | 0.15 |
| O | 13 | — | — | 70 | — | — | — | — | 29.98 | — | — | 0.02 |
| O | 14 | — | — | 30 | — | — | — | — | 69.98 | — | — | 0.02 |
| O | 15 | — | — | 70 | — | — | — | — | — | 29.98 | — | 0.02 |
| O | 16 | — | — | 30 | — | — | — | — | — | 69.98 | — | 0.02 |
| O | 17 | — | — | — | 50 | — | — | — | — | 49.98 | — | 0.02 |
| O | 18 | — | — | — | — | 100 | — | — | — | — | — | — |
| O | 19 | — | — | — | — | 99.99 | — | — | — | — | — | 0.01 |
| O | 20 | — | — | — | — | 99.9 | — | — | — | — | — | 0.1 |
| O | 21 | — | — | — | — | 99 | — | — | — | — | — | 1 |
| X | 22 | — | — | — | — | 98 | — | — | — | — | — | 2 |
| O | 23 | — | — | — | — | 50 | — | — | 50 | — | — | — |
| O | 24 | — | — | — | — | 30 | — | — | 70 | — | — | — |
| O | 25 | — | — | — | — | 10 | — | — | 90 | — | — | — |
| X | 26 | — | — | — | — | 5 | — | — | 95 | — | — | — |
| O | 27 | — | — | — | — | 50 | — | — | — | 50 | — | — |
| O | 28 | — | — | — | — | 30 | — | — | — | 70 | — | — |
| O | 29 | — | — | — | — | 50 | — | — | — | — | 49.98 | 0.02 |
| O | 30 | — | — | — | — | — | 50 | — | 50 | — | — | — |
| O | 31 | — | — | — | — | — | — | 50 | 50 | — | — | — |
| X | 32 | — | — | — | — | — | — | — | 100 | — | — | — |
| X | 33 | — | — | — | — | — | — | — | 99.98 | — | — | 0.02 |
| X | 34 | — | — | — | — | — | — | — | — | 100 | — | — |
| X | 35 | — | — | — | — | — | — | — | — | 99.98 | — | 0.02 |
| X | 36 | — | — | — | — | — | — | — | — | — | 99.95 | 0.05 |

X) The mark "0" refers to the ampholytic polymers of the present invention and the mark "X" refers to comparative examples.

The ampholytic polymers thus obtained were examined as to the absorption capacity for deionized water and aqueous electrolyte solutions by the following method. Each of the ampholytic polymers was dried, and 0.5 g of the dried polymer was immersed in 500 ml of deionized water or various aqueous electrolyte solutions for 2 hours. The immersed polymer was filtered with a 200-mesh wire net to drain water for 10 minutes. Then, the weight of the polymer having absorbed the aqueous medium on the wire net was measured, and the weight in gram of the aqueous medium absorbed in one gram of the dried polymer was defined as the absorption capacity. As the aqueous electrolyte solution, 0.5M aqueous NaCl solution, 2M aqueous NaCl solution, 0.5M aqueous $CaCl_2$ and synthetic sea water (available from Yashima Yakuhin Co., Ltd.; Aquamarine S). For comparison, two commercially available water-absorptive resins (marketed product A: Aquaric CA (available from Nippon Shokubai Kagaku Kogyo Co., Ltd.); and marketed product B: Aquaric CS (available from Nippon Shokubai Kagaku Kogyo Co., Ltd.) were used and measured for absorption capacity in the same manner as described above. The results are shown in Table 2.

TABLE 2

| | | Absorption capacity (g/g dried polymer) | | | | |
|---|---|---|---|---|---|---|
| X | Polymer | Deionized water | 0.5M NaCl | 2M NaCl | 0.5M $CaCl_2$ | Synthetic seawater[1] |
| X | 1 | 3 | dissolved | dissolved | dissolved | dissolved |
| O | 2 | 3 | 41 | 44 | 37 | 39 |
| O | 3 | 3 | 65 | 70 | 59 | 61 |
| O | 4 | 2 | 32 | 34 | 26 | 25 |
| O | 5 | 7 | 26 | 33 | 28 | 27 |
| X | 6 | 3 | 10 | 11 | 9 | 8 |
| O | 7 | 265 | 77 | 81 | 78 | 80 |
| O | 8 | 298 | 42 | 41 | 30 | 35 |
| O | 9 | 326 | 33 | 26 | 22 | 25 |
| X | 10 | 342 | 11 | 9 | 7 | 9 |
| O | 11 | 54 | 53 | 51 | 49 | 50 |
| O | 12 | 28 | 51 | 55 | 51 | 51 |

TABLE 2-continued

| | | Absorption capacity (g/g dried polymer) | | | | |
|---|---|---|---|---|---|---|
| X | Polymer | Deionized water | 0.5M NaCl | 2M NaCl | 0.5M CaCl$_2$ | Synthetic seawater[1] |
| O | 13 | 286 | 104 | 118 | 100 | 111 |
| O | 14 | 265 | 75 | 82 | 71 | 74 |
| O | 15 | 71 | 99 | 108 | 100 | 94 |
| O | 16 | 19 | 79 | 75 | 84 | 91 |
| O | 17 | 20 | 42 | 45 | 39 | 46 |
| O | 18 | 224 | — | — | — | 58 |
| O | 19 | 197 | — | — | — | 56 |
| O | 20 | 98 | — | — | — | 43 |
| O | 21 | 72 | — | — | — | 28 |
| X | 22 | 25 | — | — | — | 12 |
| O | 23 | 440 | — | — | — | 54 |
| O | 24 | 486 | — | — | — | 50 |
| O | 25 | 427 | — | — | — | 31 |
| X | 26 | 410 | — | — | — | 11 |
| O | 27 | 143 | — | — | — | 49 |
| O | 28 | 75 | — | — | — | 43 |
| O | 29 | 289 | — | — | — | 55 |
| O | 30 | 402 | — | — | — | 53 |
| O | 31 | 316 | — | — | — | 36 |
| X | 32 | 350 | — | — | — | 8 |
| X | 33 | 350 | 8 | 5 | 5 | 6 |
| X | 34 | 18 | — | — | — | 18 |
| X | 35 | 19 | 19 | 17 | 15 | 16 |
| X | 36 | 183 | — | — | — | 21 |
| marketed product A[2] | | 294 | 16 | 6 | 5 | 7 |
| marketed product B[3] | | 112 | 23 | 17 | 14 | 17 |

[1] Aquamarine S available from Yashima Yakuhin Co., Ltd.
[2] Aquaric CA available from Nippon Shokubai Kagaku Kogyo Co., Ltd.
[3] Aquaric CS available from Nippon Shokubai Kagaku Kogyo Co., Ltd.
X The mark "O" refers to the ampholytic polymers of the present invention and the mark "X" refers to comparative examples.

Polymer 1 is a crosslinked polymer of DMEPS as an ampholytic vinyl monomer (A) of the sulfobetaine type. As shown in Table 2, this polymer was dissolved in all the aqueous electrolyte solutions because DMEPS has no self-crosslinkability and the amount of crosslinkable monomer (C) was under the scope of the present invention, and it is, therefore, not preferred as a water-absorptive resin. Polymers 6 and 22 were obtained by the use of a crosslinkable monomer (C) in an amount over the scope of the present invention. As can be seen from Table 2, these polymers are not preferred because of their low absorption capacity. Polymers 10 was prepared by the use of an ampholytic vinyl monomer (A) in an amount under the scope of the present invention. Polymer 26 was prepared by the use of an ampholytic vinyl monomer (A) in an amount under the scope of the present invention and a non-ampholytic vinyl monomer (B) in an amount over the scope of the present invention. As shown in Table 2, these polymers have high capacity for absorbing deionized water but remarkably decreased absorption capacity for aqueous electrolyte solutions, and they are, therefore, not preferred. Polymers 32–33, 34–35 and 36 are crosslinked polymers of AA, AAm and AMPS, respectively, which were prepared without using any ampholytic vinyl monomer (A). As shown in Table 2, these polymers have high absorption capacity for deionized water but low absorption capacity for aqueous electrolyte solutions. In particular, polymers 32 and 33 have remarkably low absorption capacity, which are not preferred for applications requiting the absorption of brine. Marketed products A and B also have low absorption capacity for aqueous electrolyte solutions.

In contrast to these polymers as comparative examples, polymers 2–5, 7–9, 11–21, 23–25 and 27–31 which are included in the scope of the present invention have excellent capacity for absorbing aqueous electrolyte solutions. Further, polymers 7–9, 13, 14, 18, 19, 23–25, 27 and 29–31 have excellent absorption capacity even for deionized water. In cases where the ampholytic vinyl monomer (A) is copolymerized with the water-soluble non-ampholytic vinyl monomer (B), the absorption capacity for deionized water and various aqueous electrolyte solutions can be controlled by its monomer composition and the use of inexpensive monomers is advantageous from an economical point of view. In particular, DAPPS, DMPPS, DAPMB and DMPMB having strongly hydrophilic amide linkage in their molecules are preferred because the use of these monomers as the ampholytic vinyl monomer (A) gives an ampholytic polymer having improved absorption capacity as compared with the case where a monomer having no amide linkage is used. Polymers 18, 23–28, 30–32 and 34 were prepared without using any crosslinkable monomer (C). These polymers were crosslinked by heating during the polymerization or at the time of drying after the polymerization; therefore, they cause no dissolution or flowing even after the water absorption, and retain the strength as a gel. In such a case, there is no particular need to use any crosslinkable monomer (C).

The ampholytic polymers of the present invention as described above have excellent capacity for absorbing aqueous electrolyte solutions such as blood, sweat and urine, as well as aqueous electrolyte solutions of high concentration such as sea water and aqueous solutions of multivalent metal salts. Therefore, the ampholytic polymers of the present invention can exhibit excellent effects in many applications requiring the absorption of various aqueous electrolyte solutions, such as absorbents used in paper diapers or sanitary products; water-retaining materials, soil-conditioners and water-stop materials for agricultural or horticultural use.

What is claimed is:

1. An ampholytic polymer capable of absorbing an aqueous electrolyte solution, which is obtainable by polymerization of a monomer mixture comprising (A) 10 mol % or more of an ampholytic vinyl monomer selected from the group consisting of:

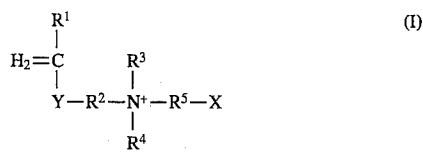

wherein $R^1$ is hydrogen or methyl; $R^2$ is a straight-chain or branched $C_1$–$C_6$ alkylene or hydroxyalkylene; $R^3$ and $R^4$ are independently methyl or ethyl; $R^5$ is straight-chain or branched $C_1$–$C_{10}$ alkylene or hydroxyalkylene; X is —COO⁻ or —SO₃⁻; and Y is an ester or amido linkage; and

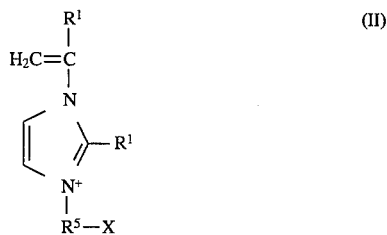

wherein $R^1$ and $R^5$ are each as defined above and X is —COO⁻ (B) 90 mol % or less of a non-ampholytic vinyl monomer comprising at least one selected from the group consisting of acrylic acid and its alkali salt and (C) 1 mol % or less of a cross-linkable monomer with the proviso that the total amount of monomers (A), (B) and (C) is 100 mol % and when the monomer (A) has no self-crosslinkability, the amount of monomer (A) is in the range of 10 to 99.995 mol % and the amount of monomer (C) is in the range of 0.005 to 0.1 mol %; the absorption capacity for synthetic seawater of said polymer being at least 25.

2. An ampholytic polymer according to claim 1, wherein the crosslinkable monomer (C) is at least one of multifunctional radical-polymerizable monomers which are crosslinkable in the radical polymerization and monomers having a functional group which is post-crosslinkable alter the polymerization.

3. An ampholytic polymer according to claim 2, wherein the monomer having a functional group which is post-crosslinkable after the polymerization is selected from monomers having carboxyl, amido, nitrile, methylol, glycidyl, hydroxyl and imino groups, and acid anhydride monomers.

4. An ampholytic polymer according to claim 1, wherein the ampholytic vinyl monomer (A) is selected from (meth) acrylamide monomers of the formula (I) wherein Y is amido; $R^3$ and $R^4$ are both methyl; and $R^5$ is $C_1$–$C_3$ alkylene.

5. An ampholytic polymer according to claim 1, wherein the ampholytic vinyl monomer (A) is selected from carboxybetaine monomers of the formula (I) wherein X is —COO⁻ or of the formula (II).

6. An ampholytic polymer according to claim 1, wherein the ampholytic vinyl monomer (A) is selected from N,N-dimethyl-N-(3-acrylamidopropyl)-N-(carboxy methyl)ammonium internal salt, N,N-dimethyl-N-(3-methacrylamidopropyl)-N-(carboxymethyl)ammonium internal salt, N,N-dimethyl-N-(3-acrylamidopropyl)-N-(carboxyethyl)ammonium internal salt and N,N-dimethyl-N-(3-methacrylamidopropyl)-N-(carboxyethyl)ammonium internal salt.

* * * * *